United States Patent [19]

Venturello et al.

[11] Patent Number: 5,245,075
[45] Date of Patent: * Sep. 14, 1993

[54] PEROXY CARBOXYLIC AMINO DERIVATIVES

[75] Inventors: Carlo Venturello, Novara; Claudio Cavallotti, Milan, both of Italy

[73] Assignee: Ausimont S.r.l., Italy

[*] Notice: The portion of the term of this patent subsequent to May 26, 2009 has been disclaimed.

[21] Appl. No.: 803,721

[22] Filed: Dec. 9, 1991

Related U.S. Application Data

[63] Continuation of Ser. No. 269,366, Nov. 10, 1988, abandoned.

[30] Foreign Application Priority Data

Nov. 13, 1987 [IT] Italy ................. 22619 A/87

[51] Int. Cl.$^5$ ................. C07C 409/24; C07C 409/28; C07C 409/38; C07C 409/40
[52] U.S. Cl. ................. 560/302; 252/100; 252/102; 252/186.42; 558/44; 562/2; 562/114; 564/281
[58] Field of Search ................. 562/2, 114; 252/100, 252/102, 186.42; 560/302

[56] References Cited

U.S. PATENT DOCUMENTS

| | | | |
|---|---|---|---|
| 3,988,433 | 10/1976 | Benedict | 424/53 |
| 4,904,406 | 2/1990 | Darwent et al. | 252/102 |
| 5,117,049 | 5/1992 | Venturello et al. | 562/2 |

OTHER PUBLICATIONS

Aoyanagi et al., *Chemical Abstracts*, vol. 11, No. 176804q (1989).

*Primary Examiner*—José G. Dees
*Assistant Examiner*—B. Frazier
*Attorney, Agent, or Firm*—Morgan & Finnegan

[57] ABSTRACT

Amino-derivative (poly)peroxycarboxylic acids which have the formula:

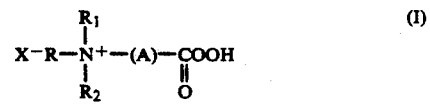

wherein the symbols have the following meanings:
R, $R_1$, and $R_2$, which may be equal to or different from one another, represent hydrogen atoms, alkyl groups or groups selected from R, $R_1$ and $R_2$, which taken together with the nitrogen atom to which they are linked, give rise to an aliphatic heterocyclic group, all of them being optionally substituted;
A represents a (cyclo) alkylene group, an arylene group which may also be condensed with cycloaliphatic groups, a cycloalkylene-alkylene or an alkylene-cycloalkylene group, an arylene-alkylene or an alkylene-arylene group, which may be condensed with cyclo-aliphatic groups wherein said alkylene group may also be interrupted by —$CONR_3$ groups, wherein $R_3$ represents a hydrogen atom or an alkyl or aryl group;
$X^-$ represents $HSO_4^-$ or $CH_3SO_3^-$; a process for their preparation; and their use as bleaching agents.

21 Claims, No Drawings

PEROXY CARBOXYLIC AMINO DERIVATIVES

This is a continuation of co-pending application Ser. No. 07/269,366, filed on Nov. 10, 1988, now abandoned.

DESCRIPTION OF THE INVENTION

The present invention relates to per se new organic (poly)peroxyacids, which can be referred to as (poly)-peroxy carboxylic amino-derivative acids, and to a process for their preparation.

More particularly, the present invention relates to (poly)peroxycarboxylic amino derivative acids having the formula (I)

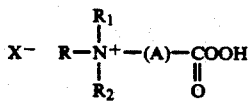

wherein the symbols have the following meanings:

R, $R_1$ and $R_2$, which may be equal to or different from one another, represent hydrogen atoms, alkyl groups or two groups selected from R, $R_1$ and $R_2$, which taken together with the nitrogen atom to which they are linked give rise to an aliphatic hetero-cyclic ring, all of them being optionally substituted;

A represents a (cyclo)-alkylene group, an arylene group which may be also condensed with cyclo-aliphatic groups, a cyclo-alkylene-alkylene or an alkylene-cyclo-alkylene group, an arylene-alkylene or an alkylene-arylene group which may also be condensed with cyclo-aliphatic groups, wherein said alkylene group may also be interrupted by —$CONR_3$ groups, wherein $R_3$ represents a hydrogen atom or an alkyl or aryl group;

$X^-$ represents $HSO_4^-$ or $CH_3SO_3^-$ to a process for their preparation, and to their use as bleaching agents.

The peroxycarboxylic amino derivative compounds having the above formula (I) are per se novel, and constitute a new class of products that are highly interesting from an industrial viewpoint.

They may, in fact, find a general use, similarly to that already known for other peroxyacids, in the field of plastics, as starter agents in the monomer polymerization and specially as oxidizing agents for olefin epoxidation and hydroxylation, and in many other oxidative processes in the field of fine chemicals.

More specifically, the amino-derivative (poly)peroxycarboxylic acids having the above formula (I) (in which (A) alkylene group) find a particularly effective application in the field of bleaching in the detergent industry.

From this point of view, generally speaking, in the past years organic peroxyacids aroused an increasing interest in the industrial field, due among others to their excellent possibilities for use as bleaching agents in formulations for medium-low temperature washing, and even more widespreadly due to energy-saving considerations.

Therefore, a large number of literature references exists concerning organic peroxyacids compounds endowed with the necessary requisites of bleaching activity, and, in particular, of thermal stability and storage stability or shelf life, these latter requisites of course being essential for industrial-scale operations and for a widespread application of such compounds.

Therefore many either mono- or di-peroxycarboxylic, straight or cyclic, organic peroxyacids are already known and used, among others, in the field of detergents.

Previously described peroxycarboxylic acids are, e.g.: diperoxydodecanedioic acid, monoperoxyphthalic acid, diperazelaic acid, and substituted diperoxyglutaric and adipic acids, etc.

Particularly, the inventors are not aware of amino-derivative (poly)peroxycarboxylic acids having the above-defined formula (I), nor of any process for their preparation.

The peroxycarboxylation process contemplates carrying out the oxidation of the substrate (an organic acid or ester) with a concentrated $H_2SO_4$ or $CH_3SO_3H$.

Therefore the strong acidity of the reaction medium and the presence in the starting substrate of a salifiable nitrogen atom of basic character confer on the said substrate a high solubility in the acidic medium.

Such high solubility, as can be easily foreseen and as verified by the present inventors, makes it impossible to apply any of the traditional processes for the isolation of the peroxycarboxylic acid derivative which may be formed in the oxidation reaction with hydrogen peroxide. In particular, the usually adopted methods of precipitation from the reaction mixture by means of a strong dilution with water, or by means of extraction with an organic solvent selective for the peroxycarboxylic acid product and immiscible with the residual reaction mixture, turn out to be impracticable.

Surprisingly, it has been discovered in accordance with the present invention that the (poly)peroxycarboxylic amino derivative acids having the formula (I), salified on the nitrogen atom with the $HSO_4^-$ or the $CH_3SO_3^-$ anion, may be obtained by a novel process which is also a part of the present invention.

Therefore, an object of the present invention is to provide as per se novel compounds, the amino-derivative (poly)peroxycarboxylic acids having the above formula (I).

Another object of the present invention is to provide a simple and cheap process for the preparation of the above peroxy carboxylic acids having the formula (I), in a per se stable form.

A further object of the present invention is the use of the peroxycarboxylic amino-derivative acids having the above formula (I) as bleaching agents in detergent formulations, and especially those intended for low-medium temperature use.

These, and still other objects which will become even clearer for those skilled it the art from the following detailed disclosure, are achieved, according to the present invention, by the (poly)peroxycarboxylic amino-derivative acids having the above formula (I), and by the relevant preparation process, characterized in that a substrate selected from a (poly) carboxylic amino-derivative acid and its quaternary salt having a structure corresponding to the desired peroxycarboxylic acids having formula (I), is reacted with concentrated $H_2O_2$, by operating in a. reaction medium selected from concentrated $H_2SO_4$ and $CH_3SO_3H$, and in that the peroxycarboxylic acid (I) is then separated from the reaction mixture by the addition of an organic solvent selected from tetrahydrofuran and ethyl acetate.

In this way the peroxycarboxylic acids having the formula (I) are obtained, generally as stable solids, salified on their nitrogen atom with the $HSO_4^-$ or $CH_3SO_3^-$ anion, optionally already present on the substrate which is used as the starting material or deriving from the reaction medium, by their insolubilization in the reaction medium by the solvent.

Described in a more detailed way, the process according to the present invention consists or consists essentially in the peroxycarboxylation reaction of the substrate consisting or consisting essentially of the (poly) acid, optionally already quaternized on the N-atom (corresponding to the desired (poly)peroxycarboxylic acid of formula (I)), in an acid medium of concentrated $H_2SO_4$ or $CH_3SO_3H$ with $H_2O_2$, and in the subsequent addition at the end of the reaction of a suitable organic solvent, which is not miscible with the desired product by dissolving it, and which is capable, on the contrary, of completely dissolving the acid reaction medium (concentrated $H_2SO_4$ or $CH_3SO_3H$), as well as the excess of $H_2O_2$ with the reaction water. This involves the consequent separation, by insolubilization, of the desired (poly)peroxycarboxylic acid product having the formula (I).

As stated above, the substrate, which is used as the starting material, corresponding to the (poly)peroxycarboxylic acid having formula (I), may be constituted by an amino-derivative carboxylic acid optionally already quaternized on the nitrogen atom.

The substrates used as the starting material are per se known compounds and/or can be prepared according to conventional techniques.

More precisely, starting compounds which already contain the quaternized N-atom generally constitute per se known products and/or may be prepared according to known techniques. Nevertheless when the substrate at least one term among R, $R_1$ and $R_2$ is a hydrogen atom, it has been found to be advantageous, from the operating point of view, to proceed to the previous preparation (under the form of $HSO_4^-$ or $CH_3SO_3^-$) by operating, in the absence of $H_2O_2$, under the same conditions a reported above for the peroxycarboxylation reaction, and by separating the thus-obtained quaternary product salt which is then peroxidated. When at least one term among R, $R_1$ and $R_2$ is a hydrogen atom, the use in the peroxidation reaction of the previously quaternized starting substrate product turns out to be advantageous in the presence of particular substrates.

The thus-obtained product is then filtered, washed with the solvent, dried, and so forth, according to the per se known techniques.

With reference to formula I, as above defined, R, $R_1$ and $R_2$, equal to or different from one another, are hydrogen atoms or linear or branched alkyl groups preferably containing from 1 to 5 carbon atoms; two of such groups, moreover, taken together with the nitrogen atom to which they are linked, may give arise to a hetero-cycloaliphatic ring containing from 4 to 6 carbon atoms. Said groups may in turn contain substituents consisting of one or more atoms or groups, either equal to or different from each another, inert under the reaction conditions under which the preparation takes place and/or in the presence of the active peroxycarboxylic oxygen, such as e.g., F or Cl atoms, OH, $NO_2$ groups, lower alkoxy groups, carboxylic groups, and so forth.

As indicated above, A represents a linear or branched alkylene group $(CH_2)_m$ wherein m represents an integer from 1 to 20, and preferably from 1 to 15, or A represents a cycloalkylene group $(C_3-C_{12})$ In addition, A may be an arylene $(C_6-C_{14})$ group or a cycloalkylene-alkylene group having the formula $(C_3-C_{12})$ cycloalkylene $—(CH_2)n$ or $(CH_2)$ alkylene-cycloalkylene $(C_3-C_{12})$; wherein n is an integer selected from 1 to 5, or of an arylene having the formula $(C_6-C_{14})$ arylene—$(CH_2)n$ or $(CH_2)n—(C_6-C_{14})$ arylene wherein n has the same meaning and the arylene part in these groups may be fused with cyclo-aliphatic groups.

The groups represented by the symbol A may be also substituted with one or more groups such as have been described for the R, $R_1$ and $R_2$ groups.

Finally, when A is a linear or branched alkylene chain group or contains such a group, said chain may be interrupted by a $CONR_3$ group wherein $R_3$ represents a lower $(C_1-C_5)$ alkyl group, an aryl group or a hydrogen atom.

Starting substrates for obtaining the corresponding amino-derivative (poly)peroxycarboxylic acids having formula (I), are, for exemplary purposes: 4-amino-butyric acid, 3-amino-propionic acid, (carboxymethyl)-trimethylammonium hydroxide or chloride (or mono-hydrated betaine), 3-piperidine-propionic acid, 11-amino-undecanoic acid, 12-amino-dodecanoic acid, glycyl-glycine, 3-amino-benzoic acid, 5-amino-isophthalic acid, 4-amino-phenylacetic acid, 5-amino-valeric acid, 6-amino-caproic acid, L-aspartic acid; N,N-dimethylamino-lauric acid, N,N-dimethylamino-undecanoic acid.

According to a preferred operating mode, the peroxycarboxylation reaction of the amino-derivative carboxylic acids used as the starting substrates, or of their quaternary salts, is carried out by gradually adding $H_2O_2$, having a concentration within the range of from approximately 70% to approximately 90% by weight, to a solution of the substrate in concentrated $H_2SO_4$ or $CH_3SO_3H$, and by maintaining the reaction temperature throughout the reaction within the range of from 15° to 50° C., depending on the reactivity of the substrate.

The amount of $H_2SO_4$ or of $CH_3SO_3H$, determined at a concentration of 100%, is not less than 2 moles, e.g. between 2 and 30 moles, per mole of substrate, and is preferably between about 7 and 10 moles per mole of substrate.

The hydrogen peroxide is used in an amount which is in excess with respect to the substrate, and is not less than 1 mole, e.g., between approximately 1 and 6 moles per mole of substrate, and preferably between 1.2 and 2 moles per mole of substrate.

The reaction time depends on the nature of the substrate, on the operating temperature, and on the total $H_2SO_4/H_2O$ or $CH_3SO_3H/H_2O$ molar ratio present at the end of the reaction. Said ratio is not less than 1.5, e.g., between approximately 1.5 and 10, and preferably between approximately 4 and 6, by adjusting the various parameters.

Reaction times between approximately 30 minutes and 4 hours have been shown to be operative, and generally it is sufficient to employ a reaction time of from approximately 1 hour to approximately 2 hours.

The amount of tetrahydrofuran or ethyl acetate solvent used is usually not lower than 4 liters/substrate mole, and furthermore, it is added at a temperature not higher than approximately 10° C.

The amino-derivative peroxycarboxylic acid products having formula (I) are usually solid at room temperature. They may be especially useful in formulations of detergent compositions, e.g. granular formulations, or as bleaching agents in solution for use over a wide temperature range.

The detergent compositions may be formulated according to the usual pertinent formulation techniques, together with other components and/or additives, etc.

Finally, the final reaction mixture, before separation of (poly)peroxycarboxylic acids of formula (I) may be subjected to a per se well known phlegmatization process.

EXAMPLES

The present invention is disclosed in still further detail in the following examples, which are supplied for purely illustrative and not limiting purposes.

The products prepared in the examples were characterized by elemental analysis, by determining their content of active oxygen (by iodometric titration), and by using Fourier Transform Infrared Spectroscopy (FT-IR).

Examples 5, 6, and 12 were carried out on a substrate separately salified.

Example 1

30 g (0.312 mole) of methanesulphonic acid were charged into a beaker equipped with stirrer, thermometer and outer bath.

The internal temperature was increased to 35°–40° C. and 4 g (0.0387 mole) of 4-amino-butyric acid were added under stirring for 15 minutes).

The above temperature was maintained until a complete dissolution of the amino-carboxylic acid was obtained, and then the temperature was lowered to 15° C. and 3.2 g of $H_2O_2$ at 85% (0.08 mole) were gradually added under stirring so that the temperature was maintained lower than 25° C. The stirring was continued for 1.5 hours at 20°–25° C.

At the end, the reaction mixture was then poured into 300 ml of tetrahydrofuran (THF) maintained under stirring at 0°–10° C.

After 1 hour of stirring, the separated product was filtered over a porous septum, washed with THF (2×30 ml), then with ethyl ether Et20 (2×30 ml), and finally was kept inside a $CaCl_2$-drier under vacuum at room temperature for 1 hour.

7.5 g of practically pure crystalline 4-amino-perbutyric acid methanesulphonate were obtained. Yield: 89.8%.

Elemental Analysis Computed for $C_5H_{13}O_6NS$: C, 27.90%; H: 6.08%; N: 6.50%; O (active): 7.43%; $CH_3SO_3H$, 44.65%. Found: C: 27.99%; H: 6.00%; N: 6.49%; O (active): 7.42% $CH_3SO_3H$: 43.13%. Melting Point: 44° C. (with decomposition).

By operating in the same way, 5-amino-pervaleric acid methanesulphonate and 6-amino-percaproic acid methanesulphonate were prepared by starting from the corresponding substrates.

5-amino-pervaleric acid methanesulphonate: computed O (active): 6.98%; found O (active): 6.80%.

6-amino-percaproic acid methanesulphonate: computed and found O (active): 6.57%.

Example 2

2 g (0.0224 mole) of 3-amino-propionic acid were completely dissolved in 15 g of $H_2SO_4$ at 96% (about 0.146 mole) and, by operating according to the procedures of Example 1, then treated with 1.8 g of $H_2O_2$ at 85% (0.045 mole), by continuing then the stirring for 1 hour. At the end, always following the operating procedures of Example 1, the reaction mixture was poured into 200 ml of THF, by then proceeding as above reported.

4 g of crystalline substantially pure 3-amino-perpropionic acid sulphate were obtained. Yield: 87.8%.

Elemental Analysis: Computed for: $C_3H_9O_7NS$: C: 17.73%; H: 4.46%; N: 6.89%; O (active): O: 7.87%; $H_2SO_4$: 48.27%. Found: C: 18.02%; H: 4.79%; N: 6.91%; O (active): 7.86%; $H_2SO_4$: 47.98%.

Example 3

By operating according to the procedures of Example 1, 3 g (0.0222 mole) of trimethyl ammonium (carboxymethyl) hydroxide (betaine monohydrate) were completely dissolved into 30 g of $H_2SO_4$ at 96% (0.292 mole) and then treated with 3 g of $H_2O_2$ at 85% (0.075 mole), in such manner as to maintain the temperature at 30° C., continuing then the stirring at 30° C. for 4 hours. At the end, by operating according to the procedure of Example 1, the reaction mixture was poured into 400 ml of THF, then proceeding as above described.

4.2 g of crystalline trimethyl-ammonium-(percarboxymethyl) bisulphate were obtained, having a purity of 90% (active oxygen content of 6.22%; theoretical value 6.92%), corresponding to a yield of 73.7%.

Elemental Analysis: Computed for: $C_5H_{13}O_7NS$: C: 25.97%; H: 5.66%; N: 6.06%; O (active): 6.92%; $H_2SO_4$: 45.42%. Found: C: 25.96%; H: 5.72%; N: 6.1%; O (active): 6.22%; $H_2SO_4$: 45.89%. Melting Point: 52° C. (with decomposition).

Example 4

By operating according to the procedures of Example 1, 4.7 g (0.0287 mole) of 3-piperidine propionic acid were dissolved into 36 g (0.374 mole) of methanesulphonic acid and then treated with 6 g of $H_2O_2$ at 70% (0.123 mole), so as to maintain the temperature at 20° C., continuing then the stirring at 15°–20° C. for 1 hour. At the end (always by operating according to the procedure of Example 1), the reaction mixture was poured into 400 ml of THF, and by proceeding then as above described.

7.2 g of crystalline substantially pure 3-piperidine-perpropionic acid methanesulphonate were obtained. Yield: 93%.

Elemental Analysis: Computed for $C_9H_{19}O_6NS$: C: 40.13%; H: 7.11%; N: 5.20%; O (active): 5.94%; $CH_3SO_3H$: 35.68%. Found: C: 39.73%; H: 6.94%; N: 5.08%; O (active); 5.93%; $CH_3SO_3H$: 35.9%. Melting Point: 132° C. (with decomposition).

Example 5

5 g (0.0248 mole) of 11-amino-undecanoic acid were slowly and under stirring added to 15 g of methanesulphonic acid into a 50 ml beaker, care being taken to maintain the temperature at 40° C. by using a cooling bath; the stirring was then continued at 35°–40° C. up to complete dissolution.

The mixture was then poured into 150 ml of ethyl acetate maintained under stirring at 10° C. The stirring was continued for 30 minutes. The precipitated 11-amino-undecanoic acid methanesulphonate was filtered over a porous septum, washed first with ethyl acetate (2×30 ml), then with $Et_2O$ (2×30 ml), then dried under vacuum at room temperature over $CaCl_2$. 7 g of product were obtained.

6.6 g (0.0222 mole) of 11-amino-undecanoic acid methanesulphonate were dissolved into 13 g of $CH_3SO_3H$ at room temperature. 1.1 g of $H_2O_2$ at 85% (0.0275 mole) were slowly added under stirring, so as to maintain the temperature at 15° C., continuing then the stirring for 30 minutes at 10°–15° C.

At the end, by operating according to the procedures of Example 1, the reaction mixture was poured into 300 ml of ethyl acetate, by proceeding as above described.

4.9 g of crystalline substantially pure 11-amino-perundecanoic acid methanesulphonate were obtained. Yield: 70.4%.

Elemental Analysis: Computed for: $C_{12}H_{27}O_6NS$: C: 45.98%; H: 8.68%; N: 4.46%; O (active), 5.10%; $CH_3SO_3H$: 30.66%. Found: C: 45.83%; H: 8.78%; N: 4.48%.; O (active): 5.09%; $CH_3SO_3H$: 30.79%. Melting Point: 63° C. (with decomposition).

Example 6

5 g (0.0232 mole) of 12-amino-dodecanoic acid were treated according to the procedure of Example 5 with 25 g of $CH_3SO_3H$.

The above reported procedure was followed except by using tetrahydrofuran instead of ethyl acetate. 6.7 g of 12-amino-dodecanoic acid methanesulphonate were obtained.

8.3 g (0.0267 mole) of 12-amino-dodecanoic acid methanesulphonate were dissolved into 16 g of $CH_3SO_3H$ at ambient temperature.

1.3 g of $H_2O_2$ at 85% (0.0325 mole) were slowly added under stirring, by operating according to the procedure of Example 5.

At the end, the operating procedures of Example 1 were followed, and 8 g of crystalline and substantially pure 12-amino-perdodecanoic acid methanesulphonate were obtained Yield: 91.4%.

Elemental Analysis: Computed for $C_{13}H_{29}O_6NS$: C: 47.68%; H: 8.93%; N: 4.27%; O (active): 4.88%; $CH_3SO_3H$: 29.35%. Found: C: 47.08%; H: 8.82%; N: 4.25%; O (active): 4.87%; $CH_3SO_3H$: 29.21%. Melting Point: 92° C. (with decomposition).

Example 7

By operating according to the procedure of Example 1, 5 g (0.0378 moles) of glycyl-glycine were completely dissolved into 25 g of $CH_3SO_3H$ and then treated with 3.6 g of $H_2O_2$ at 85%, continuing then the stirring at 20°–25° C. for 2 hours.

Continuing further according to the procedures of Example 1, and using 400 mol of THF, 8.8 g of crystalline glycyl-amino-peracetic acid methanesulphonate were separated, having a purity of 91.5% (active oxygen content of 5.99%; theoretical value: 6.55), corresponding to a yield of 87.2%.

Elemental Analysis: Computed for $C_5H_{12}O_5N_2S$: C: 24.59%; H: 4.95%; N: 11.47%; O (active): 6.55%; $CH_3SO_3H$: 39.35%. Found: C: 24.58%; H: 5.32%; N: 11.51%; O (active): 5.99%; $CH_3SO_3H$: 39.20%. Melting Point: 97° C. (with decomposition).

Example 8

The procedures of Example 1 were repeated, by substituting 4-amino-butyric acid with 3-amino-benzoic acid (4 g; 0.0291 mole) and by using 2.9 g of $H_2O_2$ at 85% (0.0725 mole) instead of 3.2 g.

6.6 g of crystalline 3-amino-perbenzoic acid methanesulphonate were obtained having a purity of 98%. Yield: 89.8%.

Elemental Analysis: Computed for $C_8H_{11}O_6NS$: C: 38.55%; H: 4.45%; N: 5.62%; O (active): 6.42%; $CH_3SO_3H$: 38.55%. Found: C: 39.0%; H: 4.22%; N: 5.62%; O (active): 6.29%; $CH_3SO_3H$: 37.9%.

The product decomposed at 114° C. without melting.

Example 9

The procedures of Example 8 were repeated, by substituting 3-amino-benzoic acid with 5-amino-isophthalic acid (2 g: 0.011 mole) and by using 32 g of $CH_3SO_3H$ instead of 30 g, 2.7 g of $H_2O_2$ at 85% (0.0675 mole) instead of 2.9 g, and ethyl acetate (800 ml) instead of THF.

3.1 g of crystalline and substantially pure 5-amino-diperisophthalic acid methanesulphonate were obtained. Yield: 91%.

Elemental Analysis: Computed for: $C_9H_{11}O_9NS$: C: 34.95%; H: 3.58%; N: 4.53%; O (active): 10.34%; $CH_3SO_3H$: 31.07%. Found: C: 34.96%; H: 3.85%; N: 4.30%; O (active): 10.33%; $CH_3SO_3H$: 30.96%.

The product decomposed at 122° C. without melting.

Example 10

The procedures of Example 8 were repeated, by substituting 3-amino-benzoic acid with 4-amino-phenyl-acetic acid (3 g: 0.0198 mole) and by using 19 g of $CH_3SO_3H$ instead of 30 g, 2.2 g of $H_2O_2$ at 85% (0.055 mole) instead of 2.9 g, and ethyl acetate (300 moles) instead of THF.

5.2 g of crystalline and substantially pure 4-amino-phenyl-peracetic acid methanesulphonate were obtained. Yield: 98.5%.

Elemental Analysis: Computed for $C_9H_{13}O_6NS$: C: 41.06%; H: 4.98%; N: 5.32%; O (active): 6.07%; $CH_3SO_3H$: 36.5%. Found: C: 40.71%; H: 5.24%; N: 4.95%; O (active) 6.00%; $CH_3SO_3H$: 35.82%.

The product decomposed at 134° C. without melting.

Example 11

The procedure of Example 2 were repeated by substituting sulphuric acid with methanesulphonic acid (15 g; 0.156 mole).

4.4 g of crystalline and substantially pure 3-amino-perpropionic acid methanesulphonate were obtained. Yield: 98%.

Elemental Analysis: Computed for $C_4H_{11}O_6NS$: C: 23.87%; H: 5.51%; N: 6.96%; O (active): 7.95%; $CH_3SO_3H$: 47.76%. Found: C: 23.88%; H: 5.66%; N: 6.70%; O (active): 7.95%; $CH_3SO_3H$: 48.02%.

EXAMPLE 12

5 g (0.056 mole) of 3-amino-propionic acid were slowly added under stirring to 15 g of sulphuric acid into a 50 ml beaker, care being taken to maintain the temperature at 40° C. by using a cooling bath. The stirring was then continued at 35°–40° C. up to complete dissolution.

The mixture was then poured into 150 ml of tetrahydrofuran, maintained under stirring at 10° C. The stirring was continued for 30 minutes.

The separated 3-amino-propionic acid sulphate was filtered over a porous septum, washed first with tetrahydrofuran (2×30 ml), then with $Et_2O$ (2×30 ml), then dried under vacuum at room temperature over $CaCl_2$.

The procedures of Example 2 were repeated by substituting 3-amino-propionic acid with the thus-obtained 3-amino-propioninc sulphate (4.18 g, 0.0224 mole). Analogous results were obtained.

Example 13

The procedures of Example 3 were repeated by substituting (carboxymethyl) trimethyl ammonium hydroxide with the corresponding chloride (3.41 g; 0.0222 mole). Analogous results were obtained.

Example 14

5 g (0.0248 mole) of 11-amino-undecanoic acid were transformed into the corresponding sulphate by operating as described in Example 5, but by substituting methanesulphonic acid with sulphuric acid. 6.5 g of product were obtained.

6 g (0.0201 mole) of the thus-obtained 11-amino-undecanoic acid sulphate were dissolved into 9 g of $H_2SO_4$ at 96% (0.0882 mole) at room temperature. 2.1 g of $H_2O_2$ at 85% (0.0525 mole) were then slowly added under stirring, so as to maintain the temperature at 15° C., continuing then the stirring for 30 minutes at 10°-15° C. At the end, by operating according to the procedures of Example 1, the reaction mixture was poured into 300 ml of ethyl acetate, proceeding as above described.

6 g of crystalline and substantially pure 11-amino-perundecanoic acid sulphate were obtained. Yield: 95%.

The composition was confirmed by the elemental analysis. O (active): computed 5.07%; found 5.04%.

By operating according to an analogous procedure 12-amino-perdodecanoic acid sulphate was prepared.

O (active): computed 4.85%; found 4.85%.

Example 15

15 g of $H_2SO_4$ at 96% (0.147 mole) were charged into a beaker equipped with stirrer, thermometer and outer bath. The internal temperature was kept at 0° C. and, under agitation and during 10 minutes, 4.8 g of $H_2O_2$ at 85% (0.12 mole) were added by maintaining the isotherm at a temperature lower than +5° C. Then 6 g of L-aspartic acid (0.045 mole) were added so that the temperature was maintained at 15° C. The stirring was continued at 15° C. for 1 hour.

At the end, the reaction mixture was poured into 250 ml of ethyl acetate maintained under stirring at 0° C. After 30 minutes of stirring at this temperature, the crystalline separated product was filtered over a porous septum, under vacuum, and washed with 2×30 ml of ethyl acetate and then with 2×30 ml of ethyl ether. The product was then dried for 1 hour under vacuum, at room temperature in a $CaCl_2$ drier.

8.5 g of crystalline and substantially pure 2-aminomono-persuccinic acid sulphate were obtained. Yield: 76%.

Elemental Analysis: Computed for: $C_4H_9O_9NS$: C: 19.43%; H: 3.67%; N: 5.66%; O (active): 6.47%; $H_2SO_4$ 39.67%. Found: C: 19.43%; H: 3.88%; N: 5.63%; O (active): 6.46%; $H_2SO_4$ 39.1%. Melting Point: 98° C. (with decomposition).

Example 16

By operating according to the procedures for Example 1, 2 g of $H_2O_2$ at 85% (0.05 mole) were added, under stirring, to 6.3 g of $H_2SO_4$ at 96% (0.0617 mole) so as to maintain the temperature at ≦5° C. 2 g of 4-aminobutyric acid (0.0194 mole) were slowly added to maintain the temperature lower than +10° C. The stirring was continued for 30 minutes at 10° C. At the end, by operating according to the procedures of Example 1, the reaction mixture was poured into 60 ml of ethyl acetate, maintained under stirring at 0° C., by proceeding as above-reported.

3.8 g of crystalline substantially pure 4-amino-perbutyric acid sulphate were obtained. Yield: 90%.

Elemental Analysis: Computed for: $C_4H_{11}NSO_7$: C: 22.12%; H: 5.1%; N: 6.45%; O (active): 7.36%; $H_2SO_4$: 45.15%. Found: C: 22.22%: H: 5.32%; N: 6.39% (active): 7.35%; $H_2SO_4$: 44.93%. Melting Point: 40° C. (with decomposition).

Example 17

By operating according to the procedures of Example 1, 3 g (0.0229 mole) of 6-amino-caproic acid were added, under stirring at 0°-5° C., to a mixture of 7.5 g of $H_2SO_4$ at 96% (0.0734 mole), and 2.4 g of $H_2O_2$ at 85% (0.06 mole), so as to maintain the temperature at 10° C.

The stirring was continued for 30 minutes at 10° C. The reaction mixture as poured into 100 ml of ethyl acetate, by proceeding as in Example 1.

4 g of crystalline substantially pure 6-aminopercaproic acid sulphate were obtained. Yield: 71%.

Elemental Analysis: Computed for: $C_6H_{15}NSO_7$: C: 29.38; H: 6.16%; N: 5.71%; O (active): 6.52%; $H_2SO_4$: 39.99%. Found: C: 29.97%; H: 6.39%; N: 5.69%; O (active): 6.51%; $H_2SO_4$: 39.01%. Melting Point: 47° C. (with decomposition).

Example 18

By operating according to the procedures of Example 1, 2 g of 5-amino-valeric acid (0.0171 mole) were added to a mixture of 4.9 g of $H_2SO_4$ at 96% (0.048 mole), and 1.6 g of $H_2O_2$ at 85% (0.04 mole), maintained under stirring at 0°-5° C., so as to maintain the temperature at 10° C.

The stirring was continued for 30 minutes at 10° C. The reaction mixture was poured into 100 ml of ethyl acetate, by proceeding according to the procedure as in Example 1.

3.4 g of substantially pure 5-amino-pervaleric acid sulphate were obtained. Yield: 86%.

Elemental Analysis: Computed for: $C_5H_{12}NSO_7$: C: 25.97%; H: 5.23%; N: 6.05%; O (active): 6.92%; $H_2SO_4$: 42.41%. Found: C: 25.6%; H: 5.8%; N: 5.93%; O (active): 6.91%; $H_2SO_4$: 41.88%. Melting Point: 64° C. (with decomposition).

Example 19

3 g (0.0088 mole) of N,N-dimethylamino-lauric acid methanesulphonate were completely dissolved into 4.5 g of $CH_3SO_3H$ (0.0468 mole) at 15° C. and then treated with 0.5 g (0.0125 mole) of $H_2O_2$ at 85%, so as to maintain the temperature at 15° C. The stirring was continued for 45 minutes at 15° C. The reaction mixture was the poured into 70 ml of tetrahydrofuran maintained under stirring at −10° C.

By proceeding according to the procedures of Example 1, 1.5 g of crystalline substantially pure N-N-dimethyl-aminoperlauric acid methanesulphonate were obtained. Yield: 48%.

Elemental Analysis: Computed for: $C_{15}H_{33}NS$: C: 50.68; H: 9.35%; N: 3.94%; O (active): 4.5%; $CH_3SO_3H$: 27.03%. Found: C: 50.28%; H: 9.35%; N: 3.91%; O (active): 4.49%; CH 26.91%. Melting Point: 75° C. (with decomposition).

Example 20

2 g (0.0088 mole) of N,N-dimethyl-amino-undecanoic acid were completely dissolved into 2.9 g of $H_2SO_4$ at 96% (0.0284 mole).

0.9 g of $H_2O_2$ at 85% (0.0226 mole) were then added to the mixture under stirring at 0°–5° C., so as to maintain the temperature at 10° C.

The stirring was continued for 1 hour at 15° C. The reaction mixture was poured into 80 mol of ethyl acetate, maintained under stirring at −30° C.

By operating according to the procedures of Example 1, 2.2 g of crystalline substantially pure N-N-dimethyl-aminoperundecanoic acid sulphate were obtained. Yield: 73%.

Elemental Analysis: Computed for: $C_{13}H_{29}NSO_7$: C: 45.46; H: 8.51%; N: 4.08%; O (active): 4.66%; $H_2SO_4$ 28.55%. Found: C: 45.31%; H: 8.55%; N: 4.02%; O (active): 4.65%; $H_2SO_4$ 28.47%. Melting Point: 46° C. (with decomposition).

Example 21 (Application Example)

Bleaching tests were carried out with the novel amino-derivative peroxycarbolic acid listed in the annexed Tables 1 and 2, at an alkaline pH (Table 1) and an acid pH (Table 2), as compared to:

(a) H 48 (Mg salt of monoperphthalic acid), a commercial peroxyacid known in the detergent art, and manufactured by INTEROX Chemical Ltd., London, U.K. (Tables 1 and 2).

(b) Perborate+perborate activator system, which, as known, develops a peroxyacid (peracetic acid) in situ when both products are dissolved in water and which represents the presently most widely used form for the purpose of obtaining a bleaching action at medium-low temperatures ($\leq 60°$ C.) and wherein, as the activator, TAED (tetraacetylethylenediamine) was selected, in an amount which corresponds to the stoichiometric ratio to the perborate (Table 1).

(c) sodium perborate ($NaBO_3.4H_2O$) alone (PBS) (Table 1).

All tests were carried out at constant temperature of 60° C., with an initial concentration of total active oxygen in the bleaching solution equal for all products, and equal to 200 mg/l.

Process

For each test, 500 ml of deionized water, contained in a 1,000 ml flask equipped with a condenser, was heated to a temperature of 60° C. and adjusted to a pH value of 9.5 (with a few drops of an NaOH) solution (Table 1) and to a pH 2–3 (with a few drops of diluted $H_2SO_4$) (Table 2); then the bleaching product was added with stirring with such amounts thereof being added as shown in the following Tables, and immediately thereafter, two cotton specimens of 10 cm×10 cm stained with standard stains of red wine at EMPA INSTITUTE of St. Gallen (Switzerland), and marked with the "EMPA 114" mark, were added.

The system was subsequently kept stirred for 60 minutes and, at the end of this time, the specimens, rinsed under running water, were dried and ironed, and were then subjected to an evaluation of the bleaching effect by means of measurements of whiteness degree by reflectometry; the results are reported in the following Tables 1 and 2, wherein the data are expressed as Bleaching %, defined as:

$$\text{Bleaching \%} = \frac{A-B}{C-B} \times 100$$

wherein:

A=degree of whiteness (%) of the specimen bleached after the test;

B=degree of whiteness (%) of the specimen before the test;

C=degree of whiteness (%) of the completely bleached specimen and wherein the degrees of whiteness were measured by means of an Elrepho Zeiss reflectometer, assuming MgO=100% of whiteness, and using filter N.6 ($\lambda$=464 nm).

The data listed in Table 1, which are tests carried out at an alkaline pH, show that the peroxyacids of the present invention have a bleaching power which may be compared with the bleaching power of H 48 and in some cases even higher.

Likewise, the results, expressed as bleaching %, listed in Table 2, show that the products proved to have a bleaching power in acid solution particularly high and very much higher than that of H 48.

This is particularly surprising in consideration of the fact that the peroxide compounds generally show a bleaching activity very modest and sometimes negligible at acid pH.

TABLE 1

| | Tests Carried out at Alkaline pH (9.5) | | |
|---|---|---|---|
| Compound | Amounts used in the tests (grams) | Initial concentration of total active oxygen (mg/l) | Bleaching (%) |
| Example 4 (titer = 5.93% of active oxygen) | 1.69 | 200 | 76.7 |
| Example 7 (titer = 5.99% of active oxygen) | 1.67 | 200 | 74.3 |
| Example 6 (titer = 4.87% of active oxygen) | 2.05 | 200 | 44.9 |
| Example 3 (titer = 6.22% of active oxygen) | 1.61 | 200 | 72.8 |
| Example 11 (titer = 7.95% of active oxygen) | 1.26 | 200 | 67.7 |
| Example 1 (titer = 7.42% of active oxygen) | 1.35 | 200 | 83.3 |
| H 48 (titer = 5.5% of active oxygen) | 1.82 | 200 | 82.1 |
| PBS (titer = 10% of active oxygen) + TAED | 1.0 + 0.8 | 200 | 79.7 |
| PBS (titer = 10% of active oxyen) | 1.0 | 200 | 68.8 |

TABLE 2

| | Tests Carred Out at Acid pH (2-3) | | |
|---|---|---|---|
| Compound | Amounts used in the tests (grams) | Initial concentration of total active oxygen (mg/l) | Bleaching (%) |
| Example 4 (titer = 5.93% of active oxygen) | 1.69 | 200 | 84.3 |
| Example 7 | 1.67 | 200 | 82.8 |

TABLE 2-continued

| | Tests Carred Out at Acid pH (2-3) | | |
|---|---|---|---|
| Compound | Amounts used in the tests (grams) | Initial concentration of total active oxygen (mg/l) | Bleaching (%) |
| (titer = 5.99% of active oxygen) | | | |
| Example 6 | 2.05 | 200 | 79.9 |
| (titer = 4.87% of active oxygen) | | | |
| H 48 | 1.82 | 200 | 60.0 |
| (titer = 5.5% of active oxygen) | | | |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The references are hereby incorporated by reference.

What is claimed is:

1. Amino-derivative of peroxycarboxylic acids having the formula

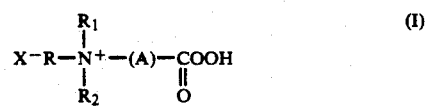

wherein the symbols have the following meanings:

R, $R_1$ and $R_2$, which may be the same or different from each other, represent hydrogen atoms, alkyl groups or alkyl groups substituted by at least one substituent selected from the group consisting of F, Cl, OH, $NO_2$, lower alkoxy, carboxylic groups, which may be equal to or different from each other;

A represents an alkylene group, cyclo-alkylene group, a cycloalkylene-alkylene or an alkylene-cycloalkylene group, which may also be fused with cyclo-aliphatic groups, wherein said alkylene group is optionally interrupted by $CONR_3$ groups, wherein $R_3$ represents a hydrogen atom or an alkyl or an aryl group; and X represents $HSO_4^-$ or $CH_3SO_3^-$.

2. Amino-derivative of peroxycarboxylic acids, according to claim 1, having formula (I), wherein R, $R_1$ and $R_2$, which may be the same or different from each other, are hydrogen atoms or linear or branched alkyl groups, containing from 1 to 5 carbon atoms.

3. N-quaternized amino-derivative of peroxycarboxylic acids, according to claim 1, having formula (I), wherein A is a linear or branched alkylene group containing from 1 to 20 carbon atoms; a cyclo-alkylene ($C_3-C_{12}$) group, a ($C_3-C_{12}$) cyclo-alkylene-($C_1-C_5$) alkylene group, or a ($C_1-C_5$) alkylene-($C_3-C_{12}$) cyclo-alkylene group.

4. Amino-derivative peroxycarboxylic acids, according to claim 3, wherein the branched alkylene group contains from 1 to 15 atoms.

5. Amino-derivative of peroxycarboxylic acids, according to claim 1, or 3 wherein A is an alkylene chain or contains an alkylene chain, and said chain may be interrupted by —$CONR_3$-groups, wherein $R_3$ represents a hydrogen atom or a lower alkyl or aryl group.

6. A N-quaternized compound as defined in claim 1, which is 4-aminoperbutyric acid methanesulphonate.

7. A N-quaternized compound as defined in claim 1, which is 3-amino-perpropionic acid sulphate.

8. A N-quaternized compound as defined in claim 1, which is (percarboxymethyl)-trimethyl-ammonium bisulphate.

9. A N-quaternized compound as defined in claim 1, which is 11-amino-perundecanoic acid methanesulphonate.

10. A N-quaternized compound as defined in claim 1, which is 12-amino-perdodecanoic acid methanesulphonate.

11. A N-quaternized compound as defined in claim 1, which is 3-amino-perpropionic acid methanesulphonate.

12. A N-quaternized compound as defined in claim 1, which is 5-amino-pervaleric acid methanesulphonate.

13. A N-quaternized compound as defined in claim 1, which is 6-amino-percaproic acid methanesulphonate.

14. A N-quaternized compound as defined in claim 1, which is 12-amino-perdodecanoic acid sulphate.

15. A N-quaternized compound as defined in claim 1, which is 11-amino-perundecanoic acid sulphate.

16. A N-quaternized compound as defined in claim 1, which is 5-amino-perbutyric acid sulphate.

17. A N-quaternized compound as defined in claim 1, which is 6-amino-percaproic acid sulphate.

18. A N-quaternized compound as defined in claim 1, which is 5-amino-pervaleric acid sulphate.

19. A N-quaternized compound as defined in claim 1, which is N,N-dimethyl-amino-perlauric acid methanesulphonate.

20. A N-quaternized compound as defined in claim 1, which is N,N-dimethyl-amino-perundecanoic acid sulphate.

21. A detergent formulation having as active bleaching agent an amino-derivative peroxycarboxylic acid having the formula (I) of claim 1, plus carriers or ingredients used in commercial detergent formulations.

* * * * *